United States Patent [19]

Willemse

[11] Patent Number: 5,231,199

[45] Date of Patent: Jul. 27, 1993

[54] PROCESS FOR THE SYNTHESIS OF POLYOL FATTY ACID POLYESTERS

[75] Inventor: Gerardus W. Willemse, Vlaardingen, Netherlands

[73] Assignee: Van den Bergh Foods Co., Division of Conopco, Inc., Lisle, Ill.

[21] Appl. No.: 870,166

[22] Filed: Apr. 16, 1992

Related U.S. Application Data

[63] Continuation of Ser. No. 372,404, Jun. 27, 1989, abandoned.

[30] Foreign Application Priority Data

Jun. 29, 1988 [GB] United Kingdom ................. 8815426

[51] Int. Cl.$^5$ ............................................... C09F 5/00
[52] U.S. Cl. ..................................... 554/174; 554/161
[58] Field of Search ............................... 554/174, 161

[56] References Cited

U.S. PATENT DOCUMENTS

| | | | |
|---|---|---|---|
| 3,963,699 | 6/1976 | Rizzi et al. | 536/119 |
| 4,517,360 | 5/1985 | Volpenhein | 536/119 |
| 4,518,772 | 5/1985 | Volpenhein | 536/119 |
| 5,006,648 | 4/1991 | Van der Plank et al. | 536/119 |
| 5,071,975 | 10/1991 | Van der Plank et al. | 536/119 |

*Primary Examiner*—Paul J. Killos
*Attorney, Agent, or Firm*—Gerard J. McGownan, Jr.

[57] ABSTRACT

The invention pertains to a process for the synthesis of polyol fatty acid polyesters, in which a polyol and/or a fatty acid oligoester thereof, is esterified by reaction with fatty acid lower alkylester under substantially solvent-free conditions at elevated temperature in the presence of a transesterification catalyst and, optionally an emulsifier, and in which at least during the final stage of the transesterification reaction the reaction mixture is submitted to the action of a stripping agent suitable for accelerating the removal of the lower alkyl alcohol formed in said reaction. The process is of particular advantage in the synthesis of polyesters of very high degrees of conversion.

20 Claims, No Drawings

PROCESS FOR THE SYNTHESIS OF POLYOL FATTY ACID POLYESTERS

This is a continuation of Ser. No. 07/372,404 filed Jun. 27, 1989, abandoned.

The present invention relates to a process for the synthesis of polyol fatty acid polyesters, in which a polyol and/or a fatty acid oligoester thereof, is esterified by reaction with fatty acid lower alkylester under substantially solvent-free conditions at elevated temperature and reduced pressure in the presence of a transesterification catalyst and, optionally an emulsifier. The invention in particular, although not exclusively, relates to a process for the synthesis of sugar fatty acid polyesters, such as sucrose fatty acid polyesters.

Polyol fatty acid polyesters, and in particular, the sugar fatty acid polyesters, such as e.g. the sucrose fatty acid poly-esters, are known as suitable low-calorie fat-replacers in edible products. Substantially indigestible for human beings they have physical and organoleptic properties very similar to triglyceride oils and fats conventionally used in edible products. In addition, polyol fatty acid polyesters are reported to have use as pharmaceutical agents e.g. in view of their ability to take up fat-soluble substances, such as in particular cholesterol, in the gastro-intestinal tract, and subsequently remove those substances from the human body.

In this specification the term "polyol" is intended to include any aliphatic or aromatic compound which comprises at least four free hydroxyl groups. Such polyols in particular include the group of sugar polyols, which comprises the sugars, i.e. the mono-, di and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, maltose, lactose, cello-biose, raffinose, sucrose, erythritol, mannitol, lactitol, sorbitol, xylitol and alphamethylglucoside. A generally used sugar polyol is sucrose.

In this specification the term "polyol fatty acid polyester" is intended to include any such polyesters or mixtures thereof of which, on an average, at least 70% of the polyol hydroxyl groups have been esterified with fatty acids.

In this specification the percentage of polyol hydroxyl groups of the polyol fatty acid ester that on an average have been esterified with fatty acids, will be referred to as the degree of conversion, the situation where all hydroxyl groups have been esterified corresponding to 100% conversion.

In this specification the term "fatty acid" refers to $C_8$–$C_{24}$ fatty acids which may be saturated or unsaturated, and which may have straight or branched alkyl chains.

In general polyol fatty acid polyesters are synthesized by a process in which a polyol, such as a mono- or disaccharide, is reacted with a fatty acid lower alkylester, in general a fatty acid methylester, in the presence of a transesterification catalyst, such as e.g. an alkali metal hydroxide or carbonate. In a first stage a polyol fatty acid mono- or oligoester is formed, which in a second stage is further reacted with excess fatty acid lower alkylester to form polyol fatty acid polyesters of the desired degree of esterification. Under certain conditions the two stages of the reaction can be combined into a single step.

Processes of this type are described in e.g. the U.S. Pat. No. 3,963,699, U.S. Pat. No. 4,517,360, and U.S. Pat. No. 4,518.772.

To drive the transesterification reaction towards the desired high conversion to polyol fatty acid polyester it is necessary during the reaction to continuously remove the lower alcohol formed in the transfer of fatty acid residues from the lower alkyl fatty acid ester to the polyol or polyolester. In conventional processes removal of the lower alcohol from the reaction mixture is achieved by carrying out the reaction under conditions of reduced pressure.

It has now been found that the time required by the transesterification reaction to reach high degrees of conversion can be reduced and the reaction better controlled when during, in particular, the latter stage of the reaction the removal of the lower alcohol is increased by the use of a stripping agent.

Since catalyst efficiency is adversely influenced by long reaction times, the reduction of reaction times is of advantage not only for reasons of operating time and energy consumption, but also for reason of catalyst consumption.

Accordingly, the present invention provides a process for the synthesis of polyol fatty acid polyesters, in which a polyol and/or a fatty acid oligoester thereof, is esterified by reaction with fatty acid lower alkylester under substantially solvent-free conditions at elevated temperature in the presence of a transesterification catalyst and, optionally an emulsifier characterized in that at least during the final stage of the transesterification reaction the reaction mixture is submitted to the action of a stripping agent suitable to accelerate the removal of the lower alkyl alcohol formed in said reaction.

The process in accordance with the invention is preferably applied to achieve high degrees of conversion, such as degrees of conversion of 85% and above, and in particular 95% or even 97% and above, without the need of excessive transesterification times.

Any stripping agent which under the conditions of the reaction (described hereunder in more detail) accelerates the removal of the lower alkyl alcohol and which does not adversely interfere with the transesterification reaction, can suitably be employed. Suitable such stripping agents include inert gases, such as nitrogen, and volatile (under reaction conditions) organic compounds having low or no chemical activity under reaction conditions. A particularly preferred stripping agent is hexane.

The appropriate flow of stripping agent through the reaction mixture is dependent upon the reaction conditions and the dimensions of the equipment, in particular of the reaction vessel. In general, and particularly during the final stage of the transesterification reaction, the flow of stripping agent lies within the range of 100 to 2500 liters of stripping agent per hour and per kg of reaction mixture.

The amount of stripping agent is expressed as liters under the pressure and temperature conditions of the reaction mixture at the moment of stripping. Expressed in this way, the flow ranges are independent of temperature and pressure.

Preferably, a flow of stripping agent of more than 200, in particular of between 250 and 1500 liters/hour/kg of reaction mixture is used, the range of 300 to 1000, or even 500 to 1000 liters/hour/kg being preferred most.

Suitable contact between the stripping agent and the reaction mixture is normally established due to the whirling action caused by the stripping agent flowing through the reaction mixture. However, it may be desirable to apply further agitation by way of appropriate stirrer means.

Preferably, after leaving the reaction mixture the stripping agent is first, at least partly, separated from the lower alkyl alcohol, and subsequently recirculated to the reaction mixture.

In a further preferred aspect of the invention a sufficiently volatile lower alkyl fatty ester is used as stripping agent. Suitable such volatile lower alkyl fatty acid esters are lower alkyl esters, in particular methyl esters, of fatty acids having a fatty acid chain length of less than 15 carbon atoms, in particular, of 6 to 12 carbon atoms, chain lengths of 10 to 12 carbon atoms being preferred.

The sufficiently volatile lower alkyl fatty acid ester used as stripping agent may be introduced as such during the reaction, or as part of the blend of lower alkyl fatty acid ester used as active reactant in the transesterification reaction. Suitable such blends have fatty acid residues derived from vegetable oils such as in particular the lauric fats, e.g. palm kernel oil and coconut oil, comprising a relatively large proportion of the appropriate short chain fatty acids.

The amount of lower alkyl fatty acid ester stripping agent used during the reaction, calculated as percentage by weight of the total amount of lower alkyl fatty acid ester, should be at least 5%, an amount within the range of 10 to 20% being preferred.

The transesterification reaction is suitably carried out at a temperature which normally lies within the range of from 100° to 180° C. Preferably temperatures are applied within the range of from 110° to 160° C., the range of from 120° to 150° C. being preferred most.

It has been found of advantage to control the partial vapour pressure of the lower alkyl alcohol such that in an initial stage (a) the polyol is esterified to a degree of conversion within the range of 10 to 50%, preferably within the range of 10 to 30%, substantially without leaving non-participating polyol (i.e. leaving less than about 20%, calculated by weight of the initial polyol, of any polyol material that will remain unreacted throughout the transesterification reaction), and that in a subsequent stage the reaction mixture resulting from stage (a) is further esterified in accordance with the process of the present invention.

Preferably, during the final part of stage (a) the partial vapour pressure of the lower alkyl alcohol is controlled to a level of within 30 mbar, most preferably within 15 mbar from the equilibrium vapour pressure of the lower alkyl alcohol corresponding to a degree of conversion within the range of from 10 to 30%. Accordingly, the partial vapour pressure of the lower alkyl alcohol is suitably controlled to a level within the range of from 60 to 150 mbar, preferably 90 to 125 mbar during the final part of stage (a).

During the first part of stage (a), in order to initiate the transesterification reaction quickly, it is of advantage to apply a pressure above the reaction mixture as low as technically and economically feasible, such as e.g. below 25 mbar, or even below 10 mbar. Subsequently, the pressure can be allowed to increase to the preferred levels described hereinbefore due to progressive formation of lower alkyl alcohol.

Subsequent to stage (a) the pressure is reduced to a level of below 50 mbar, and preferably to a level of below 25 mbar, such as below 15 mbar, or even below 5 mbar to remove the lower alkyl alcohol formed from the fatty acid lower alkylester as a result of the transesterification. It is in particular during the final part of this stage of the reaction that the reaction mixture is submitted to the action of the stripping agent in accordance with the invention to further assist in the removal of the lower alkyl alcohol. The action of the stripping agent is preferably started when the transesterification reaction has progressed to a degree of conversion of between 60 and 95%, and most preferably when the degree of conversion has reached a level of between 80 and 95%.

It is preferred to apply agitation to the reaction mixture, throughout the reaction e.g. by way of stirring means in the reaction vessel.

In general the reactants used as the starting mixture of the transesterification reaction in accordance with the process of the present invention comprise a polyol, optionally in combination with a fatty acid oligoester thereof, a fatty acid lower alkylester, a basic transesterification catalyst, a fatty acid alkali metal soap, and solvent, such as water and/or alcohols.

The polyol may be any of those as defined hereinbefore, or a mixture thereof. Preferred polyol starting materials are the sugar polyol, and in particular, sucrose.

Suitable fatty acid lower alkylesters are fatty acid esters of the group of lower alcohols including mono-, di- and triols. In particular, the ester is derived from the $C_1$-$C_5$ mono-alcohols, preferably methanol. The fatty acids can be any of those as defined hereinbefore, the selection of which is dependent of the specific polyol fatty acid esters desired.

The amount of fatty acid lower alkylester is dependent of the desired degree of conversion. In general an excess amount of the fatty acid lower alkylester is used. For instance, in the synthesis of 100% converted sucrose good results are obtained when a molar ratio of fatty acid lower alkylester:sucrose is used within the range of from 10:1 to 20:1.

Suitable transesterification catalysts include the group consisting of alkali metals and alkaline earth metals, and their alkoxides, bicarbonates, carbonates, hydrides, hydroxides, and their alloys. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

The catalyst is used in an amount corresponding to a molar ratio of catalyst:polyol of at least 0.01:1, preferably of 0.05:1 to 1:1.

In general an emulsifier will be used in order to improve contact between the polyol, the catalyst and the fatty acid lower alkyl ester. Many types of alkali-resistant emulsifiers can suitably be used, such as edible emulsifiers including phosphatides, such as lecithin, and detergents, such as soaps, alkali metal alkyl sulphates, and sugar oligoesters of fatty acids. It is preferred to use alkali metal soaps derived from any of the fatty acids as defined hereinbefore. The alkali metal soap may be introduced as such, but preferably the soap is prepared in-situ, for example by partial saponification of the fatty acid lower alkyl esters as used in the trans-esterification reaction or by neutralization of any fatty acids added. At in-situ preparation of the fatty acid soap it is preferred to use a solvent in which the alkaline substance used for the saponification or neutralization dissolves so as to improve contact during the saponification or neutralization reaction.

Conversion rates of polyol to polyol fatty acid ester are advantageously affected when a fatty acid soap is used preferably comprising at least 15%, or even at least 75% of short chain fatty acid soap, having a fatty acid chain length of less than 15 carbon atoms, in particular 6 to 12 carbon atoms.

A solvent is used to improve addition and mixing of the various reactants. Suitable solvents include water and/or lower alcohols, such as the $C_1$-$C_5$ alcohols.

Advantageously, intimate mixing of the reactants and simultaneous solvent removal is achieved by combining the reactants into a mixture, and passing this mixture through a spraying nozzle into a drying chamber. Intimate mixing occurs due to the dissipation of energy on passing through the spraying nozzle. Evaporation of the solvent occurs in the drying chamber, the resulting vapour continuously being removed from the drying chamber by suitable reduced pressure or gas flow conditions. Adequate solvent evaporation may be established by a variety of per se conventional techniques, including the application of reduced pressure and/or elevated temperature conditions, or the use of, optionally heated, co-current, counter-current or mixed-current inert gas flows. In a batch-wise operation the drying chamber is also suitably used as reaction vessel for the transesterification reaction. In a continuous or semi-continuous operation the drying chamber and reaction vessel preferably are separate.

It may be of further advantage to pre-mix the reactants before passing through the spraying nozzle by an alternative agitation step for example employing a dynamic or static mixer, or flow restriction in the feed line to the spraying nozzle.

It is preferred to prepare the initial mixture of reactants by way of a two-step process.

In a first step the polyol or the fatty acid oligoester thereof is mixed with the catalyst in a liquid system so as to form the corresponding polyol anion. The formation of the actual polyol anion may be immediate or only be realized under substantially solvent-free conditions. Preferably, the liquid mixture further comprises a solvent used to improve the contact between the polyol or the oligoester thereof and the catalyst. Suitable such solvents include water, lower alcohols and mixtures thereof. In particular water is a suitable solvent if potassium hydroxide or sodium hydroxide is used as the transesterification catalyst.

In the second step the liquid system is combined with the fatty acid lower alkyl ester. The fatty acid soap may be introduced into the mixture, either separately, or as part of the liquid system of step 1, or in combination with the fatty acid lower alkyl ester.

Suitably, the starting mixture of reactants resulting after step 2 is subsequently agitated and solvent is removed therefrom by a spray-drying step as described hereinbefore.

It is even more preferred first to prepare a mixture comprising the fatty acid lower alkylester and the soap emulsifier, which mixture is spray-dried before it is combined with further reactants, in particular the liquid system of step 1. By this route which accordingly comprises two spray-drying steps, optimal mixing of and solvent removal from the starting mixture of reactants is achieved by a process that can easily be applied on a technical scale and by continuous or semi-continuous operation.

If so desired a supplementary amount of polyol may be introduced to the starting mixture of reactants before starting the transesterification reaction.

The invention will now be further illustrated with reference to following example. Using a two-step spray-drying process first a reaction mixture was prepared having the following composition:

| ingredients | % by weight |
|---|---|
| methylesters of soybean oil fatty acids | 90 |
| potassium soap of coconut fatty acids | 3 |
| sucrose (25% as potassium sucrate) | 7 |
| OH-value | 90 |

In a 200 l reaction vessel fitted with stirrer, condensor and vacuum means 150 kg of this reaction mixture was caused to react to the partial sucrose ester (degree of conversion of about 20%; OH-value of 70) in 3 hours at 135° C. and 100 mbar pressure. Subsequently, the pressure was reduced to below 5 mbar (maintaining the temperature at 135° C.), the degree of conversion increasing to approximately 90% (OH-value of 9). During the final stage of the transesterification reaction at 135° C. and at about 15 mbar a flow of hexane vapour was introduced into the reaction mixture in an amount of about 120 m³/hour (corresponding to 800 liters per hour per kg of reaction mixture). After one hour of stripping ($t_1$) with hexane vapour the degree of conversion has increased to approximately 96% (OH-value of 4.5) and after two hours of stripping ($t_2$) to approximately 98% (OH-value of 2.3).

In a comparative experiment equal amounts of ingredients were used, and reacted under the same process conditions and during the same process times, but without applying a stripping agent at the final stage of the reaction. At time $t_1$ the degree of conversion now was 95% (OH-value of 5.5) and at $t_2$ the degree of conversion had reached 96%.

These comparative experiments illustrate the usefulness of the process of the invention particularly when very high degrees of conversion are aimed at, such as degrees of conversion of over 95%.

I claim:

1. A process for the synthesis of polyol fatty acid polyesters, comprising esterifying a polyol and/or a fatty acid oligoester thereof by reacting with fatty acid lower alkyl ester under substantially solvent free conditions at elevated temperature in the presence of a transesterification catalyst, and when the reaction has progressed to an average degree of esterification of between 60 and 95%, submitting the reaction mixture to the action of a stripping agent suitable for accelerating the removal of the lower alkyl alcohol formed in said reaction.

2. A process according to claim 1 in which said stripping agent is hexane.

3. A process according to claim 1 in which at least during a final stage said reaction mixture is contacted with said stripping agent at a flow within the range of 100 to 2500 liters/hour/kg of reaction mixture.

4. A process according to claim 3 in which said flow is within the range of 300 to 1000 liters/hour/kg.

5. A process according to claim 1 in which said stripping agent is a lower alkyl fatty acid ester which is volatile under the conditions of the reaction.

6. A process according to claim 5 in which the fatty acid residues of said lower alkyl ester have a fatty acid chain length of less than 15 carbon atoms.

7. A process according to claim 6 in which said fatty acid chain lengths lie within the range of 6 to 12.

8. A process according to claim 5 in which the amount of lower alkyl fatty acid ester stripping agent used in the reaction is 10 to 20% by weight of the total amount of lower alkyl fatty acid esters.

9. A process according to claim 1 in which said stripping agent is recirculated.

10. A process according to claim 1 in which during the final stage said reaction is carried out at a pressure of below 50 mbar.

11. A process according to claim 1 for the synthesis of polyol fatty acid polyesters having a degree of conversion of over 85%.

12. A process according to claim 11 for the synthesis of polyol fatty acid polyesters having a degree of conversion of over 95%.

13. A process according to claim 1 in which the action of the stripping agent is started when the transesterification reaction has progressed to a degree of conversion of between 80 and 95%.

14. The process according to claim 1 wherein the esterification reaction is conducted in the presence of an emulsifier.

15. The process according to claim 14, wherein the stripping agent is hexane.

16. The process according to claim 14 wherein at least during a final stage the reaction mixture is contacted with said stripping agent at a flow within the range of 100 to 2500 liters/hour/kg of reaction mixture.

17. The process according to claim 16 wherein said flow is within the range of 300 to 1000 liters/hour/kg.

18. The process according to claim 14 wherein the stripping agent is a lower alkyl fatty acid ester which is volatile under the conditions of the reaction.

19. The process according to claim 14 wherein the stripping agent is recirculated.

20. The process according to claim 14 wherein the polyol fatty acid polyesters synthesized have a degree of conversion of between 80 and 95%.

* * * * *

UNITED STATES PATENT AND TRADEMARK OFFICE
CERTIFICATE OF CORRECTION

PATENT NO. : B1 5,231,199
DATED : August 4, 1998
INVENTOR(S) : Willemse

It is certified that error appears in the above-identified patent and that said Letters Patent is hereby corrected as shown below:

On the title page: Item[56]

A) "U.S. PATENT DOCUMENTS", please insert as new entries after "5,158,796 10/1992 Bernhardt", the following:

--3,963,699  6/1974  Rizzi et al.
  4,614,613  7/1984  Fikentscher et al.
  4,973,682  11/1990 Willemse--

B) "FOREIGN PATENT DOCUMENTS", please insert as new entries after "02 72 759 6/1988 European Pat. Off.", the following:

--0 132 293   European Pat. Off.
  0 320 043   European Pat. Off.
  0 227 137   German Pat. Off.
  50-135016   Japanese Pat. Off.--

C) "OTHER PUBLICATIONS", please insert as new entries after "pp. 398-401. Apr. 1978.", the following:

--October 20, 1997 Notice of Opposition filed in EP 0 349 059.
International Encyclopedia of Chemical Science, p. 1095 (D. Van Norstrand Company, Inc., 1964).--

Signed and Sealed this

Fourth Day of July, 2000

Attest:

Q. TODD DICKINSON

*Attesting Officer*            *Director of Patents and Trademarks*

REEXAMINATION CERTIFICATE (3587th)

United States Patent [19]

Willemse

[11] B1 5,231,199

[45] Certificate Issued Aug. 4, 1998

[54] PROCESS FOR THE SYNTHESIS OF POLYOL FATTY ACID POLYESTERS

[75] Inventor: Gerardus W. Willemse, Vlaardingen, Netherlands

[73] Assignee: Van Den Bergh Foods Company, Division of Conopco, Inc., New York, N.Y.

Reexamination Request:
No. 90/004,345, Aug. 28, 1996

Reexamination Certificate for:
Patent No.: 5,231,199
Issued: Jul. 27, 1993
Appl. No.: 870,166
Filed: Apr. 16, 1992

Related U.S. Application Data

[63] Continuation of Ser. No. 372,404, Jun. 27, 1989, abandoned.

[30] Foreign Application Priority Data

Jun. 29, 1988 [GB] United Kingdom .................. 8815426

[51] Int. Cl.$^6$ ....................................................... C09F 5/00
[52] U.S. Cl. ............................................ 554/174; 554/161
[58] Field of Search ................................. 554/174, 161

[56] References Cited

U.S. PATENT DOCUMENTS

| | | |
|---|---|---|
| 3,347,848 | 10/1967 | Ismail . |
| 4,348,540 | 9/1982 | Ferris . |
| 4,517,360 | 5/1985 | Volpenhein . |
| 4,518,772 | 5/1985 | Volpenhein . |
| 4,806,632 | 2/1989 | McCoy . |
| 5,158,796 | 10/1992 | Bernhardt . |

FOREIGN PATENT DOCUMENTS

| | | |
|---|---|---|
| 0 233 856 A2 | 8/1987 | European Pat. Off. . |
| 0233856 | 8/1987 | European Pat. Off. . |
| 0 272 759 AZ | 6/1988 | European Pat. Off. . |
| 0272759 | 6/1988 | European Pat. Off. . |

OTHER PUBLICATIONS

Himmelblau Basic Principles And Calculation in Chemical Engineering pp. 96–97 1967.

Himmelblau, Basic Principles and Calculations in Chemical Engineering, Second Edition, Prentice–Hall, Inc., 1967, apge 97.

Rizzi, et al., "A Solvent–free Synthesis of Sucrose Polyesters", Journal of the American Oil Chemists' Society, 55:4, pp. 398–401, Apr. 1978.

*Primary Examiner*—Paul J. Killos

[57] ABSTRACT

The invention pertains to a process for the synthesis of polyol fatty acid polyesters, in which a polyol and/or a fatty acid oligoester thereof, is esterified by reaction with fatty acid lower alkylester under substantially solvent-free conditions at elevated temperature in the presence of a transesterification catalyst and, optionally an emulsifier, and in which at least during the final stage of the transesterification reaction the reaction mixture is submitted to the action of a stripping agent suitable for accelerating the removal of the lower alkyl alcohol formed in said reaction. The process is of particular advantage in the synthesis of polyesters of very high degrees of conversion.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–12 and 13–20 is confirmed.

New claims 21–30 are added and determined to be patentable.

21. *A process for the synthesis of polyol fatty acid polyesters, comprising:*

*a) esterifying a polyol and/or a fatty acid oligoester thereof by reacting with fatty acid lower alkyl ester under substantially solvent free conditions at elevated temperature, in the presence of transesterification catalyst, such that the partial vapor pressure of the lower alkyl alcohol formed in said reaction is controlled by an applied pressure to achieve initially an average degree of esterification of between 10–50%; and*

*b) when the reaction in step a) has progressed to an average degree of esterification of between 60 and 95%, submitting the reaction mixture to the action of a stripping agent suitable for accelerating the removal of the lower alkyl alcohol formed in said reaction.*

22. *A process according to claim 21 wherein the partial vapor pressure of the lower alkyl alcohol formed in said reaction is controlled to achieve initially an average degree of esterification of between 10–30%.*

23. *A process according to claims 21 or 22 wherein, to achieve initially the average degree of esterification recited in step a), the applied pressure is first regulated below 25 mbar to initiate transesterification and subsequently regulated between 60 to 150 mbar.*

24. *A process according to claim 23 wherein, to achieve initially the average degree of esterification recited in step a), the applied pressure is first regulated below 10 mbar to initiate transesterification and subsequently regulated between 90 to 125 mbar.*

25. *A process according to claim 23 wherein, prior to submitting the reaction mixture to the action of a stripping agent in step b), the applied pressure is further regulated below 50 mbar to remove the lower alkyl ester formed.*

26. *A process according to claim 25 wherein, prior to submitting the reaction mixture to the action of a stripping agent in step b), the applied pressure is further regulated below 25 mbar to remove the lower alkyl ester formed.*

27. *A process according to claim 26 wherein, prior to submitting the reaction mixture to the action of a stripping agent in step b), the applied pressure is further regulated to below 15 mbar to remove the lower alkyl ester formed.*

28. *A process according to claim 27 wherein, prior to submitting the reaction mixture to the action of a stripping agent in step b), the applied pressure is further regulated to below 5 mbar to remove the lower alkyl ester formed.*

29. *A process for the synthesis of polyol fatty acid polyesters, comprising esterifying a polyol and/or a fatty acid oligoester thereof with fatty acid lower alkyl ester in a single stage under substantially solvent free conditions at elevated temperature in the presence of transesterification catalyst, and when the reaction has progressed to an average degree of esterification of between 60 and 95%, submitting the reaction mixture to the action of a stripping agent suitable for accelerating the removal of the lower alkyl alcohol formed in said reaction.*

30. *A process for the synthesis of polyol fatty acid polyesters, comprising esterifying a polyol and/or a fatty acid oligoester thereof with fatty acid lower alkyl ester under substantially solvent free conditions at elevated temperature in the presence of transesterification catalyst, and starting the action of a stripping agent when the transesterification reaction has progressed to an average degree of conversion of between 60 and 95%.*

* * * * *